United States Patent [19]
Weber et al.

[11] Patent Number: 5,459,032
[45] Date of Patent: Oct. 17, 1995

[54] METHOD OF CONDUCTING A NON-INSTRUMENTAL TEST TO DETERMINE CATALYST PRESENCE

[75] Inventors: Stephen G. Weber, Pittsburgh; Robert C. Elser, York; Jane N. Valenta, Pittsburgh, all of Pa.

[73] Assignee: University of Pittsburgh, Pittsburgh, Pa.

[21] Appl. No.: 188,646

[22] Filed: Jan. 28, 1994

Related U.S. Application Data

[63] Continuation of Ser. No. 822,165, Jan. 16, 1992, abandoned, which is a continuation of Ser. No. 250,319, Sep. 28, 1988, abandoned.

[51] Int. Cl.⁶ .............................. C12Q 1/00; C12Q 1/34; C12Q 1/42; C12Q 1/26
[52] U.S. Cl. ............................ 435/4; 435/18; 435/21; 435/25; 435/26
[58] Field of Search .................. 435/4, 7.1, 18, 435/21, 25, 26, 119; 514/18, 26, 191, 210, 211, 616

[56] References Cited

U.S. PATENT DOCUMENTS

| | | | |
|---|---|---|---|
| 4,066,403 | 1/1978 | Bruschi | 23/230 B |
| 4,446,231 | 5/1984 | Self | 435/7.91 |
| 4,782,016 | 11/1988 | Norton | 435/21 |

OTHER PUBLICATIONS

Rawn David, Biochemistry, pp. 235–236, 1983 Harper & Row.

Fisher Scientific Catalog 1988, #1099, 1101, 1103, 1109.

*Primary Examiner*—Michael G. Wityshyn
*Assistant Examiner*—Ralph Gitomer
*Attorney, Agent, or Firm*—Reed Smith Shaw & McClay

[57] ABSTRACT

A method and apparatus for performing an enzyme spot test without traditional instrumentation is disclosed. The method utilizes various reagents to allow the visual determination of the presence of an enzyme in a sample above a predetermined critical level. The enzyme reacts with the reagents producing a product according to a reaction which is timed by a chemical fuse. At the end of the reaction, a colored by-product is visible, the color intensity indicating that the enzyme occurs in the sample in quantities above the critical level.

31 Claims, 7 Drawing Sheets

SUBSTRATE CONCENTRATION
a to b First Order Kinetics
c to d Zero Order Kinetics

1000/T
Enzyme activity and fuse "length" as a function of temperature

METHOD OF CONDUCTING A NON-INSTRUMENTAL TEST TO DETERMINE CATALYST PRESENCE

This is a continuation of application Ser. No. 07/822,165, filed on Jan. 16, 1992, now abandoned, which was a continuation of U.S. Ser. No. 07/250,319, filed on Sep. 28, 1988, now abandoned.

FIELD OF THE INVENTION

The present invention relates to methods and apparatus for conducting enzyme spot tests, particularly those used in the diagnosis of disease.

BACKGROUND OF THE INVENTION

Much of the progress in basic chemistry has been motivated by the interest in the nature of disease in the human. Disease impairs the performance of vital functions. Diabetes, heart disease, cancer, liver ailments, and infection are just a few disorders that interfere with normal bodily functions. Since the 1950's, there has been an unprecedented growth in the number of laboratory tests available to a physician to detect such disorders. Limitations such as sensitivity, specificity, and accuracy vary from one test to the next.

Enzymes, the catalysts which promote almost all biochemical reactions, exist in all body organs, and within the cells of these organs. Healthy cells are semipermeable, allowing small molecules to pass through the cell membrane, but retaining large molecules, such as enzymes. However, as organ cells are damaged, for example, through disease, the cell's permeability increases, allowing small quantities of enzymes to leak into the blood stream, where they may be found by chemical analysis.

The determination of enzyme activity in the subject animal or human patient's body fluids (generally blood serum) leads to an appreciation of the extent and nature of organ damage. This determination is made very sensitive and highly specific by using the native catalytic properties of the enzyme molecule to convert substrate to product. In general, if a particular enzyme is present in a sample in amounts exceeding a recognized norm, this may indicate one or more physical ailments. Thus, an abnormal level of certain enzymes acts as a fingerprint for certain diseases.

In order to measure the amount of enzyme present in a sample, it is necessary to choose a particular substrate and reaction conditions that favor the evaluation of the activity of the enzyme of interest. Reaction conditions are chosen to permit the enzyme of interest to catalyze the substrate to product reaction. The substrate and other necessary chemicals are mixed with a sample containing an unknown quantity of the enzyme of interest and the reaction is allowed to proceed. The amount of product formed in a given time is proportional to enzyme concentration. For a particular enzyme, the measurement of activity may be indicative of cell damage. The measurement of enzymes that exist in only one organ provide a clear chemical indicator of that organ's health. For example, the measurement of specific heart, liver, bone, prostate and pancreatic enzymes is possible.

The determination of enzymes is most frequently performed in clinical laboratories by experienced technicians using automated instruments incorporating light absorption, fluorescence or electrochemical detection capabilities.

Enzymes possess certain characteristics not common to other types of catalysts. First, they are quite sensitive to small changes in temperature. Second, they often show sharp changes in activity as the pH of the system changes. Third, enzymes may be very specific in catalyzing a particular type of reaction. Enzymatic specificity is necessary to maintain some degree of independence of all the reactions occurring in complex organisms. Last, many enzymes differ from other catalysts in that they are more efficient. The greatest similarity that enzymes and nonbiochemical catalysts have in common is that they change the rate of the overall chemical reaction.

The rate of a chemical reaction is expressed as a change in concentration of reactant or product in a given time interval. Enzymes usually enhance reaction rates by at least a millionfold. At a constant concentration of an enzyme, the reaction rate increases with increasing substrate (reactant) concentration until a maximal velocity is reached. In contrast, uncatalyzed reactions do not show this effect.

This property of being saturable is expressed mathematically in the Michaelis-Menten Model for enzyme kinetics. Basically, "saturable" means that the velocity of the reaction being catalyzed by the enzyme is first order, or linearly dependent on substrate concentration at lower substrate concentrations, but the velocity of the reaction becomes nearly zero order, or independent of substrate concentrations, at higher substrate concentrations, or when all enzyme active sites are saturated with substrate.

The Michaelis-Menten model provides a basis for understanding the kinetic properties of many enzymes. The general reaction scheme that this model follows is:

$$E + S \underset{K_2}{\overset{K_1}{\rightleftharpoons}} ES \overset{k_3}{\longrightarrow} E + P \qquad (1)$$

An enzyme (E) combines with substrate (S) to form an enzyme substrate complex (ES). This complex can proceed to form a product (P) or dissociate to E and S. The equation (2)

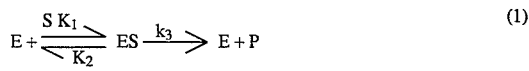

$$V = V_{Max}[S]/([S] + K_M) = \frac{k_3[E][S]}{([S] + K_m)} \qquad (2)$$

describes the rate of product formation, V. $V_{Max}$ is the maximum rate which occurs when the enzyme is fully saturated with substrate. $K_M$ is the substrate concentration at which the reaction is one half the maximal rate. Closer examination of this model reveals that the maximal velocity is the product of $k_3$ and the total enzyme concentration. $k_3$ is the turnover number that can be further defined as the number of substrate molecules converted into product per unit time. Equation (2) shows that for a given enzyme, the rate of product formation will differ for various concentrations of that enzyme.

Rates of product formation can be determined by measurement of an instrument signal that is proportional to the concentration of product. The method commonly used for measuring the concentration of product is absorption spectrometry. Some enzymatic reactions are coupled with a "coenzyme" such as NAD which when reduced to NADH absorbs light at 340 nm. The changes in the absorbance of the solution due to the NADH are monitored. The amount of NADH produced can be directly related to the activity of an enzyme present in the assay.

At high substrate concentrations, $K_M$ is $\ll[S]$ and equation 2 becomes:

$$V = V_{Max} \qquad (3)$$

This equation shows that at high substrate concentrations, the reaction velocity is zero order in S. This relationship is represented by the portion of the curve between c and d in FIG. 1. When zero order conditions prevail, the velocity of the reaction is solely determined by the concentration (activity) of the enzyme.

Zero order conditions are generally used in the measurement of enzyme concentration (when the enzyme concentration is variable) while first order conditions (section a-b in FIG. 1) are used in the measurement of reactant species (when the enzyme concentration is constant).

In order to measure V, the rate of product formation, it is necessary according to known methods to use an instrument, such as a spectrometer, which measures the change in absorptivity over time, which corresponds to the amount of enzyme in the sample.

Although the instrument measuring method performed in clinical laboratories is acceptable, there are situations in which access to a suitable laboratory and/or use of an instrument for measuring enzyme concentrations is impossible or impractical, making a non instrumental and generally extralaboratory method highly desirable. For example, non instrumental, generally extralaboratory, methods may be useful in physicians' offices, in tests performed by non-skilled individuals on themselves at home, in the field for testing animals or humans away from modern facilities, at sea, under battle conditions and in a variety of situations when testing is desirable but clinical laboratory instrumental testing methods are unavailable.

Several examples of testing may include the measurement of acetylcholinesterase (E.C. 3.1.1.8) in the blood of farmers or pesticide applicators or in the blood of soldiers exposed to nerve gas toxins, the measurement of the alanine aminotransferase (ALT, E.C. 2.6.1.2) in the blood of potential blood donors as a surrogate test for hepatitis, the measurement of amylase (E.C. 3.2.1.1) in the blood serum of sailors having abdominal pain and suspected of having pancreatitis, or the measurement of creatine kinase (E.C. 2.7.3.2) in the blood serum of persons having chest pain and suspected of having a myocardial infarction.

A non-instrumental device could be used in Third World countries lacking instrumentation, where the device would be valuable in the initial diagnosis and the monitoring of disease. Such a device could also be used for a number of different medical applications other than those dealing with disease.

SUMMARY OF THE INVENTION

The present invention comprises a non-instrumental, generally extralaboratory, system for the determination of chemically reacting species requiring kinetic measurements. This system controls the time during which any enzymatic reaction is allowed to proceed and distinguishes between various enzyme concentrations.

In kinetic measurements, the time interval of measurement is crucial, and in a non-instrumental method for the determination of enzymes or products of enzyme reactions, the time interval of measurement must be reproducibly controlled. The invention incorporates a chemical timing device or chemical "fuse" to provide control of the reaction time.

A preferred embodiment of the invention is capable of titrating a buffered sample solution using the technique of ion exchange. The addition of $H^+$ to a buffered solution containing an enzyme gradually lowers the pH of the solution and in turn causes the activity of the enzyme to change. During this acid-base titration, the enzyme remains active for a period of time, the titration time. It is during this time interval that the enzyme converts substrate to product. A color reaction has been incorporated into the device to serve as an indicator for measuring the activity of an enzyme, e.g., the formation of a tetrazolium dye product by reaction with a product of the primary enzymatic reaction. See Markert, C. L. and Moller, F., Proc. Natl. Acad. Sci. 45: 753 (1959); and Michal Gietal in Methods of Enzymatic Analysis, 3rd ed. Bergmeyer HU, ed. Vol. 1, pp. 197–232, Verlag Chemie Weinheim (1983).

In a preferred embodiment of the invention, a source of an ionic enzyme inactivator, such as $H^+$ is separated from the sample to be tested by a diffusional barrier, or spacer means, which regulates the flow of inactivator to the sample. An ionic species without enzyme inactivation properties (displacing ions), such as $K^+$, is located on the opposite side of the diffusional barrier relative to the ionic enzyme inactivator (on the same side as the sample).

To practice the invention, the enzyme-containing sample and reagents (which include displacement ions and substrate, and may include, coenzymes and other cofactors required by the enzyme, buffering ions and color reagents) are added to a reacting medium, generally the surface of the diffusional barrier distal to the ion exchange membrane. The displacement ions begin to diffuse through the diffusional barrier causing the inactivating ions to be displaced from an ion exchange membrane by the displacement ions. The inactivating ions then diffuse in the opposite direction through the diffusional barrier. [The concentration of the inactivating ions may be regulated by an optional buffer.] Meanwhile, the enzyme is catalyzing the reaction, producing product at a rate defined by the enzyme's concentration.

At some point, the enzyme becomes exposed to a high concentration of the inactivating species. At that point, enzyme activity is stopped but the product remains. The amount of product formed after the chemical "fuse" has "burned out" is proportional to the activity of the enzyme and proportional to the enzyme concentration in the sample. If the amount of product exceeds a level corresponding to a generally accepted normal level of enzyme activity, a color change occurs, which change is produced according to known methods. Alternatively, the concentration of product may be determined with standard instrumentation.

The titration time depends on the ion exchange membrane, the counterion concentration for the exchange process, the thickness of the filter separator, and lastly, the quantity of buffer being titrated.

Another aspect of the invention permits the inference of enzyme activity from the amount of product formed to be carried out with little influence of temperature. This is an important consideration for a non-instrumental test that may be carried out in uncontrolled extralaboratory conditions.

A mathematical model based on the experimental findings and theoretical considerations for ion exchange processes was constructed. The purpose of this model is to allow predictions to be made regarding the length of time an enzyme will remain active for a given set of experimental conditions. The reproducibility of this testing device was examined for some representative experimental conditions.

Other details, objects and advantages of the invention will become apparent as the following description of the presently preferred embodiments and presently preferred methods of practicing the invention proceeds.

BRIEF DESCRIPTION OF THE DRAWINGS

In the accompanying drawings, the preferred embodiments of the invention and preferred methods of practicing the invention are illustrated in which.

DETAILED DESCRIPTION OF THE INVENTION

The chemistry of the present invention is designed so that an operator using the test kit will apply a drop of blood or other sample fluid, wait, and then evaluate some characteristic change (e.g. color) indicative of the presence (or absence) of enzyme above the medical decision level.

The invention may be used to test for an enzyme E above a predetermined critical medical decision level $M_E$. The enzyme E reacts, for example, with one or more reactants a,b,c . . . , in the presence of cofactors m,n,o to yield a visible product, x,y,z, indicating the presence of E above the critical level $M_E$.

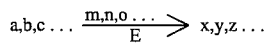

There are several methods of using the present invention according to the above reaction. One such method involves a limited activity of E. For example, it is possible to control the quantities of a,b,c . . . , m,n,o . . . so that after a given time, t, only samples for which the activity of $E>M_E$ will demonstrate visible quantities of z. It is possible to remove an amount of E corresponding to $M_E$, for example, by antibody binding, then providing sufficient a,b,c . . . , m,n,o . . . so that any remaining E is measurable.

Another method of determining the presence of $E>M_E$ involves steady state determinations. For example, if a,b,c . . . are in excess, and if one has a chemical system (say an enzyme E') for which z is a substrate, then, while E produces z, E' destroys it. Mathematics show that a concentration of z will be present at steady state which is proportional to activity of E (E' held constant). Thus a certain activity of E yields a time invariant level of z. The concentration of z becomes the critically measured quantity which is proportional to the concentration of E.

If a chemiluminescent system is coupled to the production of z, then a certain rate of change of z with time will yield a certain rate of photo-emission per time, or a constant intensity. Using a small, simple battery operated device, an intensity corresponding to $E>M_E$ can be made to give a signal.

Figure 3:
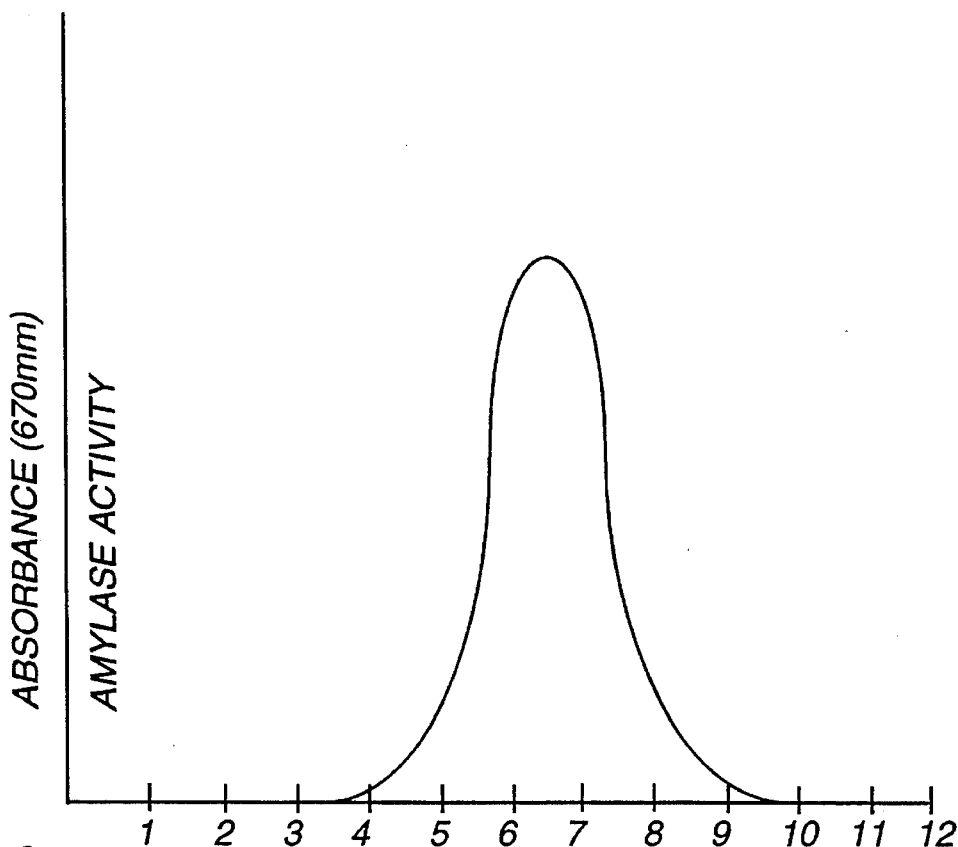
FIG. 3 is a curve illustrating enzyme activity vs. pH for amylase.

If an enzyme catalyzed reaction is carried out at a series of different pH values with the concentrations of enzyme and substrate kept constant, the rate of reaction is observed to vary, as the pH of the reaction mixture varies. As illustrated in FIG. 3, for example, the enzyme activity for amylase peaks between pH 6 and 7. This pH dependency of enzyme reactions is exploited by the present invention in the form of an acid base titration. The addition of H+ to a buffered solution containing an enzyme will gradually decrease the pH of the solution, causing the activity of the enzyme to be eventually lost. This loss of enzyme activity in turn causes the reaction to cease.

The source of H+ for the titration is provided through the means of ion exchange. NAFION, a perfluorosulfonated ion exchange membrane manufactured by E. I. DuPont, deNemours and Company, Inc., was chosen for its convenience in geometry. Of course, other ion exchange membranes could be used. In the device, the ion exchange membrane is separated from the buffered solution containing reagents and the enzyme by a filter or spacer means. Diffusion occurs through the filter. This filter lengthens the diffusional pathway through which H+ must travel before reaching the solution. The result is that the longer it takes for H+ to reach the solution, the longer an enzyme will remain active in the solution.

Enzyme activity is directly related to the quantity of product produced. Reactions of coenzymes or products that yield color in the visible region have been used as indicators for measuring the activity of an enzyme. A reaction solution's absorbance at any time during the course of the reaction depends on the activity of the enzyme. A color reaction has been incorporated into the invention for the purpose of making the change visible.

Figure 4:
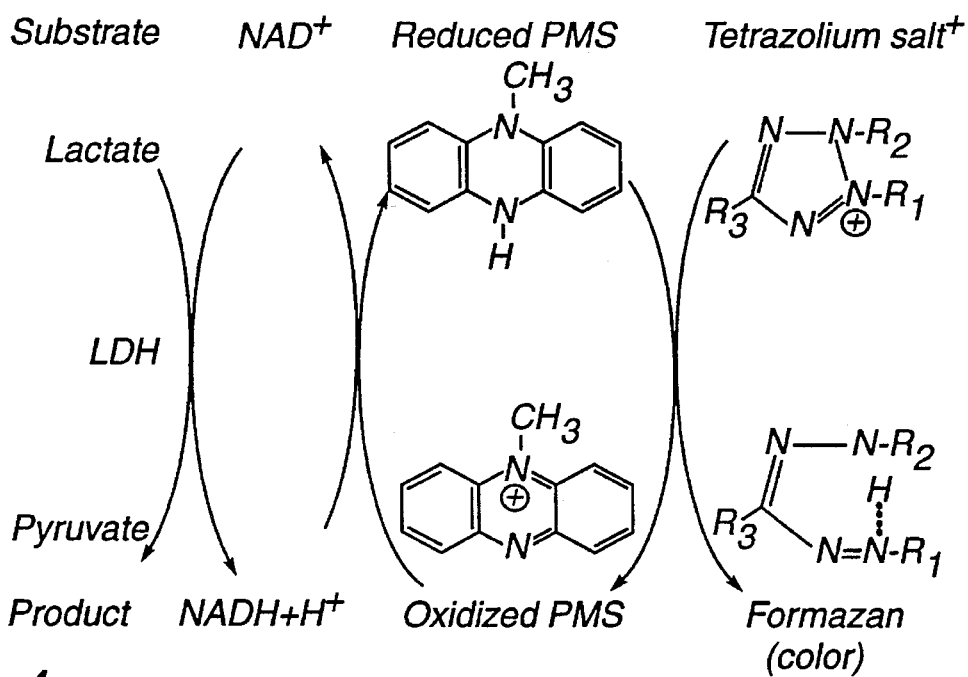
FIG. 4 is an illustration summarizing reactions useful in detecting dehydrogenase enzymes through color change.

In theory, all dehydrogenase reactions resulting in the formation of NADH can be made visible. See former reference to Bergmeyer, Vol. 1, pp. 197–232. The reduced coenzyme of nicotinamide adenine dinucleotide (NAD) can transfer hydrogen indirectly to some commonly used dyes. Synthetic compounds such as 5-methylphenazinium methyl sulfate (PMS) act as electron carriers between NADH and the dye. Tetrazolium salts are dyes which when reduced to formazans absorb light in the visible region. A summary of these reactions is shown in FIG. 4.

The resulting color from the NADH oxidation is related to the quantity of product formed in a specified time. A preferred embodiment of the present invention controls the length of time an enzyme remains active in solution. This time interval determines the quantity of NADH produced and by extension the quantity of tetrazolium salt reduced.

This can be illustrated by the equation $$dQ/dt = k_3 [E] \quad (5)$$

$$Q(t_{end}) = \int_0^{t_{end}} (dQ/dt)dt = k_3[E]t_{end} \quad (6)$$

where $Q(t_{end})$ is the quantity of NADH produced during the time interval in which the enzyme remains active, $k_3$ is a rate constant (Equation 1), and [E] is the activity of the enzyme. Therefore, enzymes with differing activity will be distinguished from one another on the basis of the quantity of product formed (for example, NADH or formazan) during the time interval in which the enzyme remains active in solution.

Figure 5:
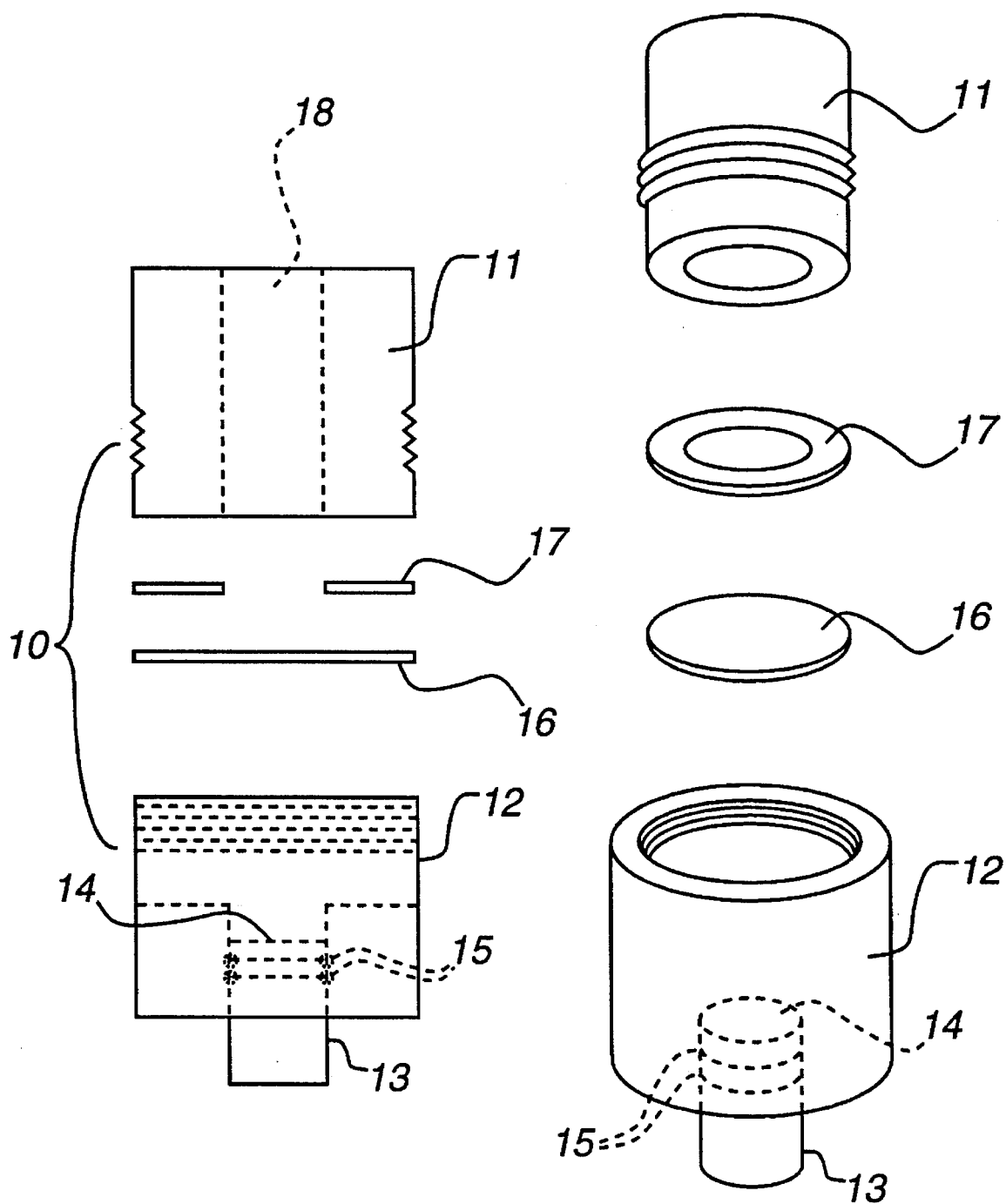
FIG. 5 is a schematic illustration of a cell used according to a preferred embodiment of the present invention.
Figure 6:
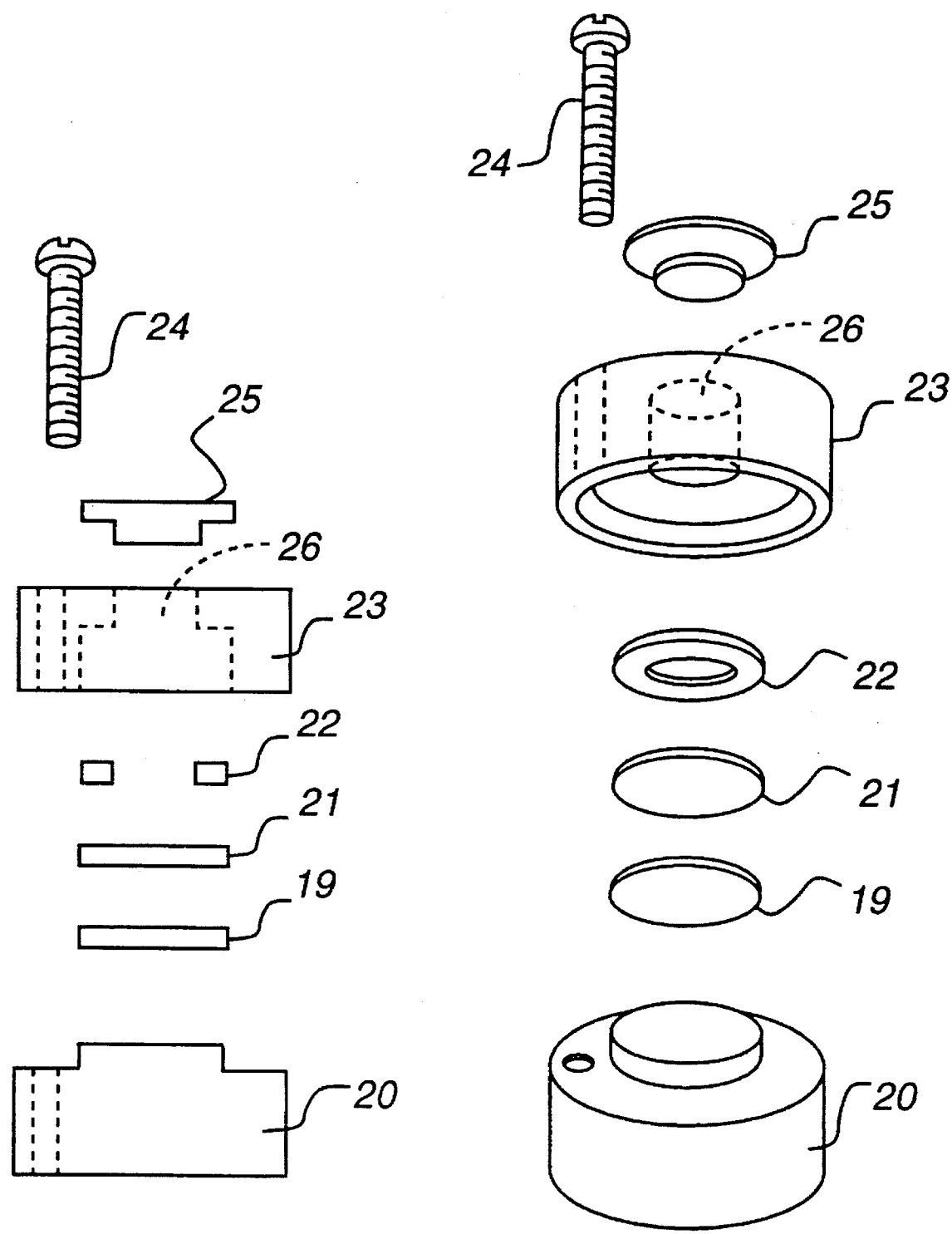
FIG. 6 is a schematic illustration of layers used according to a preferred embodiment of the present invention.

Schematic representations of "cells", generally 10, used to carry out a preferred embodiment of the invention, are shown in FIGS. 5 and 6. The use of the cell in FIG. 5 is indicated if the source of deactivating ion is a bulk material such as ion exchange resin beads, or a precipitated organic base. The use of the cell in FIG. 6 is indicated if the source of deactivating ion is a well-defined sheet of material, such as Nafion®.

The cell pictured in FIG. 5 consists of several parts, a top piece 11, which is generally cylindrical and defines a chamber or reservoir 18 in which the catalyzed reaction occurs, and which preferably screws into a base piece 12. The base, 12, has a cavity 14, which contains a plunger 13, which is used to control the volume of the cavity 14. "O" rings, 15, hold the plunger 13 securely in place within the cavity 14. The inactivating ion in an appropriate matrix, e.g. ion exchange resin beads, is held in cavity 14. Preferably, a filter or other permeable spacer means 16 covers the cavity 14. A Teflon® polytetrafluorethylene washer 17 is preferably used between the filter 16 and the top piece 11 to prevent tearing of the filter 16 when the top piece 11 is screwed into the base piece 17. When assembled, there exists a cylindrical chamber 18 defined by the top piece, 11, and the filter 16. This apparatus is stable on the shelf as long as the wet resin is stable. Insofar as we know, this is indefinite.

FIG. 6 illustrates a design for use with ion exchange membranes, rather than resin beads or a precipitated organic base. The membrane, 19 is placed, wet, onto a base plate 20. The membrane is covered with a filter or other permeable spacer means 21, and a Teflon®polytetrafluorethylene washer 22; a top piece, 23, holds the Teflon, polyretrafluorethylene filter and ion exchange membrane in place. Screws 24, may be used to secure the top piece 23 to the base plate 20. An optional cap 25 may be used to cover the top piece 23.

The diffusional barriers, 16 and 21, of FIGS. 5 and 6, respectively, separate the inactivator containing space, 14 and inactivator contains membrane 19, from the enzyme (or other catalyst) containing sample and regulate diffusion of inactivator to the sample. Any barrier serving this function may be used, and glass fits, nylon or cellulose acetate filters having 0.22 to 0.45 μm holes have proven satisfactory.

An ionic source having the same charge as the inactivator, referred to herein as "displacing ions", is placed on the opposite side of the diffusional barrier, 16 or 21, from the inhibitor, in this case in an upper reservoir 18 or 26. As used herein, the term "displacing ions" is defined to mean ions which do not inhibit enzyme activity and which displace inhibitor ions from the ion exchange medium, e.g., 19. The displacing ion source may be $K^+$ or $Mg^{+2}$, for example, and may therefore actually be an enzyme activator.

Figure 7:
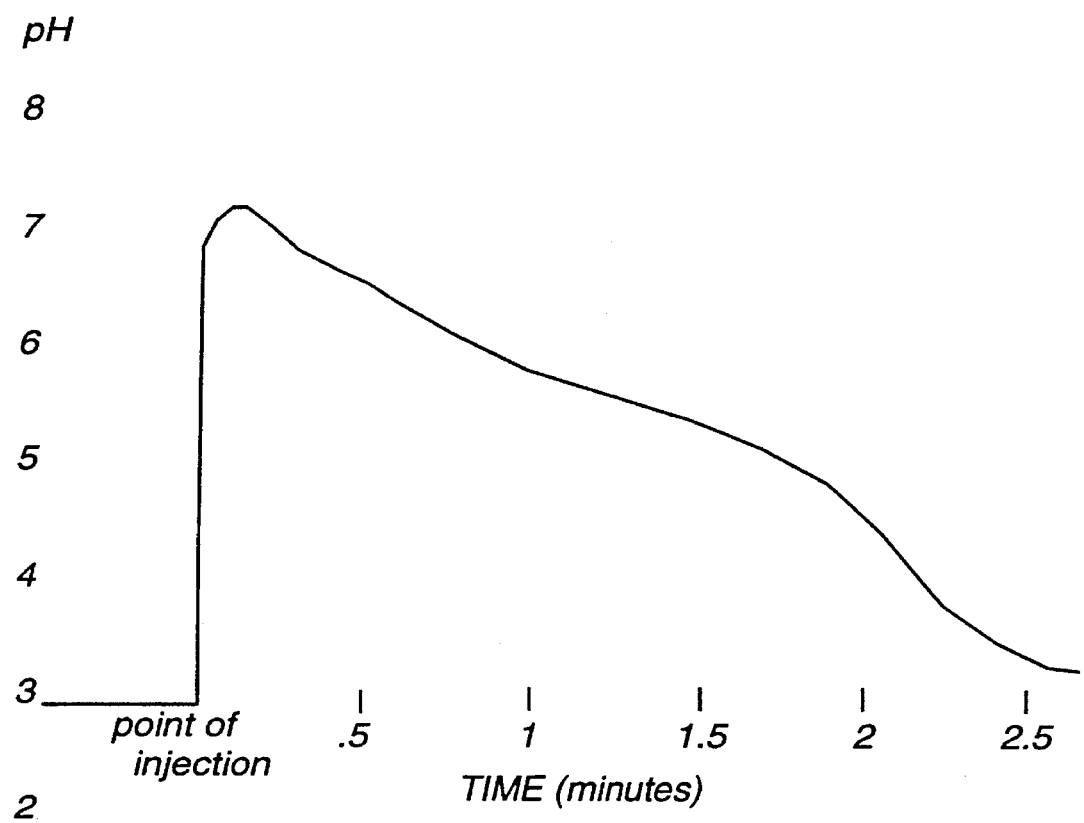
FIG. 7 illustrates a titration curve (pH vs. time) generated using a preferred embodiment of the present invention.
Figure 8:
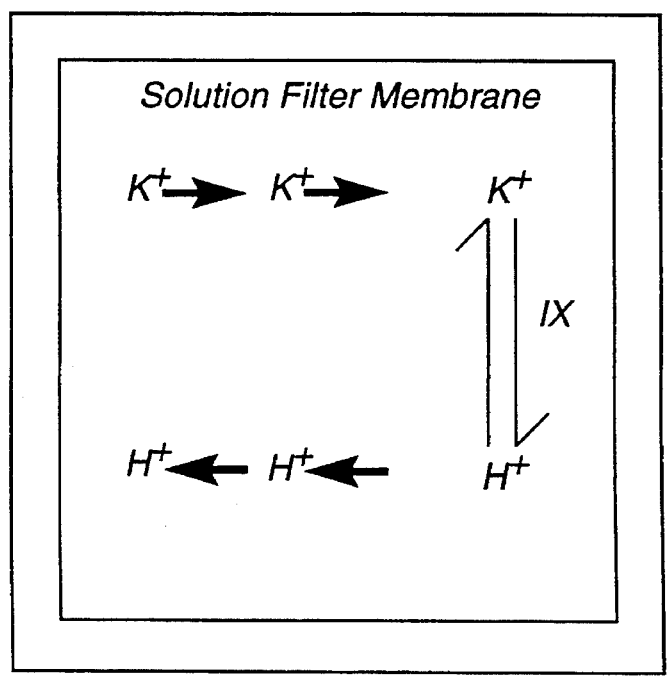
FIG. 8 illustrates the steps comprising the sequence of events responsible for controlling an enzyme's activity, and stopping an enzyme-catalyzed reaction according to the present invention.

An enzyme-containing (or other catalyst-containing) sample and reagents are introduced to in the upper reservoir 18 or 26. The reagents may be added in solution just prior to adding the enzyme-containing sample. Once the reagents and enzymes have been added, the enzyme begins to catalyze the reaction of reagents, which may include a substrate and a cofactor which participates in the color reaction. This reaction may also proceed in voids or spaces in the diffusional barriers or filter means 16 and 21. Simultaneously, the displacing ions, which are by now in solution with the reagents and enzyme sample, diffuse through the diffusional barrier 16 in a net downward direction (note that "downward" refers to the diagrams in FIGS. 5 and 6; the assistance of gravity is not required), and begin to displace inhibitor ions from the ion exchange membrane 19, or the ion exchange resin in cavity 14. As a result, inhibitor ions diffuse in the opposite direction toward the reactants and enzyme. Assuming enzyme activity is ongoing, eventually the displacing ions displace sufficient inhibitor ions such that the inhibitor ions inhibit the enzyme's activity, halting the reaction. A typical displacing ion/inhibitor displacement mechanism for a particular system is illustrated in FIG. 8. A typical time-course of the concentration of the inhibiting ion, $H^+$, (related to the pH) in the sample (upper) side can be seen in FIG. 7.

In a most preferred embodiment of the invention, the upper reservoir 18 or 26 also contains a buffer, which makes the transition of the enzyme from active to inactive much more abrupt than the transition in the absence of a buffer. The inhibitor titrates the buffer until all buffer is depleted, producing a distinct end point due to the "chemical fuse", whereby the inactivator inactivates the enzyme and halts the reaction.

The type of buffer used depends on the particular inactivator being used. For example, $H^+$ titrates basic buffers, such as $HPO_4^{-2}$; $OH^-$ titrates acidic buffers; metal ions titrate thiols or other chelating agents; and organic inhibitors titrate antibodies, metal ions or other binding media.

During the reaction time a colored product has been produced. The intensity of color visible over the (white) filter in the sample space is indicative of the enzyme activity.

There are two separate aspects to one preferred embodiment of the invention. The first, and major component is the means to achieve control over the timing. This component is essential for any embodiment of an enzyme test without instrumental or mechanical control. The second aspect, is the optimization of the color reaction to visualize the color change. This aspect is particular to each enzyme assay. It is important to note that, by optimization of the composition of the reaction medium, one can create a system in which the color intensity for a medically 'normal' sample is distinguishable from a sample from an 'abnormal' sample. These two aspects will be described sequentially.

TIMING

Principles of mass action and diffusion suggest that the titration time (or reaction time) should be 1) inversely proportional to the total weighted concentration of displacing ions initially in the upper reservoir (the weighting of concentrations depends on a particular ion's relative affinity for the ion exchange membrane), 2) proportional to the quantity of buffer in the upper reservoir, and 3) inversely proportional to the overall ion exchange rate, which depends upon upper reservoir mass transfer, separator mass transfer, ion exchange membrane mass transfer, and ion exchange kinetics.

Experimental

Ion exchange membranes were H-form Nafion 117 (Plastics Dept., DuPont Co., Wilmington, Del.) with an equivalent weight of 1100, nominal capacity of 0.91 meq/gram and thickness of 0.017 cm. Equivalent weight is defined as the mass in grams of dry polymer in the acid form to neutralize one equivalent of base. This membrane was received in the form of a sheet and pieces were cut from this sheet for the experiments. The membranes were regenerated to the H-form by soaking each membrane in a glass jar containing approximately 0.1M HCl for at least a day. Before using these membranes, they were rinsed with doubly deionized water and wiped dry.

Magna Nylon 66 filters (MSI, Honeoye Falls, N.Y.) of pore size 0.22 um were used as received. The filters have a thickness of 120 μm and a pore density of $5 \times 10^8$ pores per $cm^2$.

All chemicals used were reagent grade; all water was doubly deionized. The water was first passed through an organic removal cartridge and then passed through a high purity ion exchange cartridge with a 1 megohm automatic cutoff. The water was finally distilled in an all-glass still and stored in a Pyrex glass vessel.

Two buffer systems were employed. A phosphate buffer of pH 8 was prepared by adding 2.65 mL of 0.2M sodium phosphate monobasic, $Na_2HPO_4$ (Fisher Scientific, Fairlawn, N.J.), 47.35 mL of 0.2M sodium phosphate dibasic, $Na_2HPO_4$ (Mallinckrodt, Inc., Paris, Ky.) and diluting to 100 mL. Tris(hydroxymethyl)aminomethane Hydrochloride, TRIZMA Hydrochloride (Sigma, St. Louis, Mo.) was also prepared and was adjusted to pH 9 using a 6M NaOH solution.

Potassium Chloride, KCl (EM Science, Cherry Hill, N.J.) was reagent grade.

A diagnostic kit for Lactate Dehydrogenase, Kit No. 228-UV from Sigma (St. Louis, Mo.) was used. This test kit contained 153 umol/L of β-NAD and 50 mmol/L of L-Lactate in 106 mmol/L Tris buffer. Also purchased from Sigma were test kits containing Control Serum and Diluent (Type I-A and Type II-A) and were used as directed. Type I-A test kit contains 150 IU/L of lactate dehydrogenase while Type II-A contains 350 IU/L of lactate dehydrogenase. IU is the abbreviation for International Units. One IU is defined as the quantity of enzyme that will catalyze the reaction of one micromole of substrate per minute at 25° C. The reagents for the color reaction were Nitro Blue Tetrazolium, NBT (Sigma, St. Louis, Mo.), Phenazine Methasulphate, PMS (Sigma, St. Louis, Mo.), and Triton X-100 (Rohm & Haas, Philadelphia, Pa.).

For purposes of the experiment, the acid base titration was monitored by recording the pH changes in solution. A pH meter, an Orion Ionanalyzer Model 701 (Cambridge, Mass.) was calibrated daily using buffer solutions of pH 4 and 7 (Fisher Scientific, Fairlawn, N.J.). A Sargent-Welch recorder Model XKR (Cleveland, Ohio) was adjusted to insure that pH readings coincided with the markings on the chart paper. Since the cell is only capable of holding a small volume of solution, a pH and a reference microelectrode were purchased from Lazar Research Inc. (Los Angeles, Calif.). These electrodes can measure the pH in samples as small as 10 uL.

Employing a cell as illustrated in FIG. 6, a drop of water was placed in the cell and a wet piece of NAFION ion exchange membrane was placed into the water. To prevent the membrane from curling, additional water was placed on the membrane. A nylon filter 21, which functions as a spacer means and/or diffusional barrier, followed by the teflon ring 22 was placed onto the assembly. The top piece of the cell 23 was inserted and the entire cell was secured into place by screws 24.

The apparatus in this configuration, ready for sample and reagents is stable in a humid environment for at least 26 weeks and probably indefinitely. Other physical embodiments of this reaction vessel are certainly possible. The reaction vessel may then be incorporated into known sampling systems that have a long shelf-life. See, for example, U.S. Pat. No. 3,799,742 by Charles Coleman.

A sample solution containing 100 μL of 1:1 0.04M KCl/0.08M phosphate buffer was introduced into the cell and the pH of the solution was recorded until the solution reached a pH of 2.5. A representative titration curve is shown in FIG. 7. All measurements were made at room temperature.

The influence of the total number of ion exchange sites on titration time was determined. Each membrane was weighed before each run. The cell was assembled and 100 μL of 1:1 0.6M KCl/0.4M phosphate buffer were injected into the cell. From the experimental results obtained, a plot of titration time versus the weight of the Nafion membranes was constructed. The experimental finding was that no correlation exists between the titration time and the weight of Nafion for the given set of experimental conditions. The conclusion drawn was that each membrane contains a sufficient concentration of H+ to completely titrate the buffered solution. Even though the titration was monitored to a pH of 2.5, the titration continued on to more acidic pH's confirming that the proton reservoir was not being depleted.

The total number of ionic charges (inhibitor ions) removed from the membrane must be equal to the number of displacing ions entering the membrane. The degree or extent of exchange that occurs during this process depends mainly on the size and valence of the ions entering into the exchange and the concentration of ions in solution. The concentration ratio of two competing counterion species in the ion exchanger is usually different from that in solution. Thus, the ion exchange material selects one species over another. Studies on Nafion's selectivity toward ions have been previously investigated by Steck and Yeager, at Vol. 52 Analytical Chemistry No. 8, p. 1215–1218 (1980). Although the calculated selectivity coefficients ($K_H^M$) are for Nafion 120 (exchange capacity of 0.83 meq/gram), it is assumed that Nafion 117 would have similar selectivity coefficients for the metal ion/hydrogen ion exchange. The selectivity coefficients for the metal ion/hydrogen ion exchange of particular interest to this disclosure are listed in Table 1.

TABLE 1

| Selectivity Coefficients for Nafion 120 | |
| --- | --- |
| Ion | $K^M$ a 25° C. H |
| H+ | — |
| Li+ | .579 |
| Na+ | 1.22 |
| K+ | 3.97 |
| $Mg^{2+}$ | 2.30 |
| $Ca^{2+}$ | 3.60 |

The influence of the concentration of exchangeable displacing ion in solution was investigated, performing experiments using KCl as the displacing ion source with a concentration range between 0.06 and 0.30M. As the concentration of KCl increases, the rate of ion transfer increases as well. Therefore, if a short titration time is desired, a high concentration of displacing ion should be used. Conversely, longer titration times can be obtained by using very dilute solutions of the displacing ion.

The buffer capacity of the solution is of particular interest in studying the course of the titration. Generally, as the quantity of buffer is lowered, less H+ is needed to titrate the buffer. Differences between anionic and cationic buffers may be expected since a cationic buffer may partake in the ion exchange process as well as buffering the solution. A comparison study was done with 0.1M phosphate buffer and 0.1M Trizma buffer. Since the selectivity coefficient is not known for Trizma, it is a possibility that perhaps Trizma buffer would compete with K+ for the ion exchange sites. The experimental findings indicate that there is no apparent difference in the titration times between the 2 buffer systems. The conclusion drawn is that the Trizma buffer does not interfere with the ion exchange process even though it is positively charged.

Figure 9:
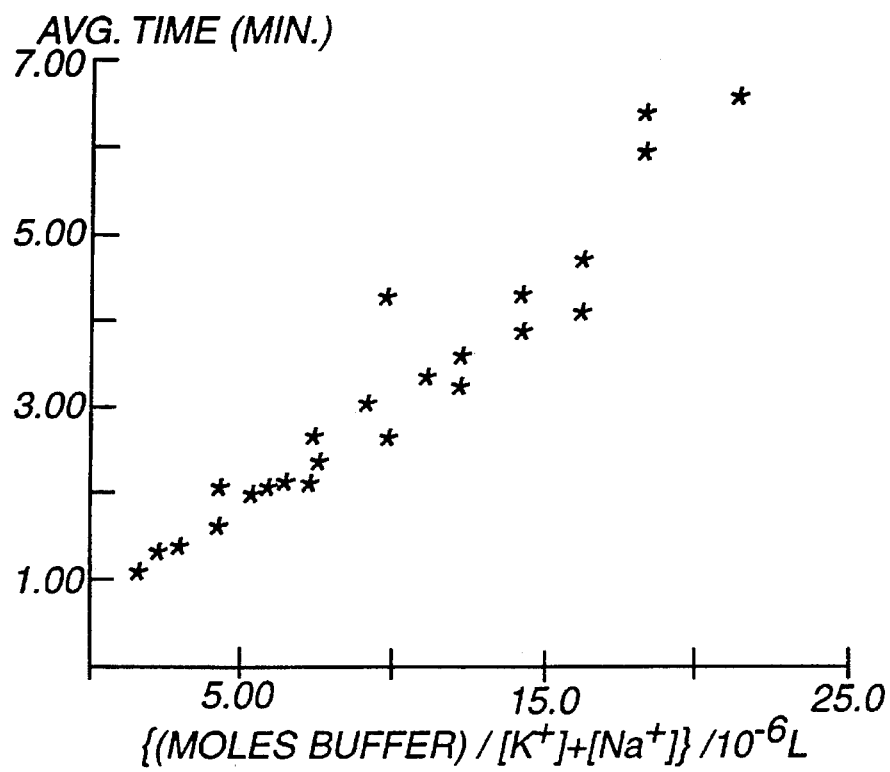
FIG. 9 illustrates a plot of average titration time versus the ratio of (total moles of buffer)/(total displacing ion concentration) for a system according to a preferred embodiment of the present invention.

For simple systems (distilled water, KCl, and buffer) the titration must therefore be proportional to the quantity <Buffer>/[$K^+$], where <> means "quantity of". Using the experimental data, a plot was constructed to examine the relationship of titration time with respect to exchangeable cation concentration and buffer quantity of the solution. For each given set of parameters, the ratio (moles of Phosphate Buffer)/[Total Concentration of Exchangeable Displacement Ion in Solution] was calculated and plotted against its corresponding average titration time. The [Total Exchangeable Displacing Ion] takes into account not only the [$K^+$] present in solution but the concentration of $Na^+$ associated with the phosphate buffer as well. This plot can be found in FIG. 9. The plot is substantially linear and the calculated correlation coefficient is approximately 0.961. FIG. 9 shows that for simple systems, the above relationship holds. However, the system becomes more complex when serum is added to the system.

Human serum contains several buffer systems; the major one being a bicarbonate/carbonic acid buffer system. The influence of these additional buffering systems was investigated. Based on these investigations, it was concluded that serum makes a significant contribution to the buffering capacity of the system, requiring addition of a larger volume of acid titrant to reach a given pH than is required when no serum is present.

Figure 10:
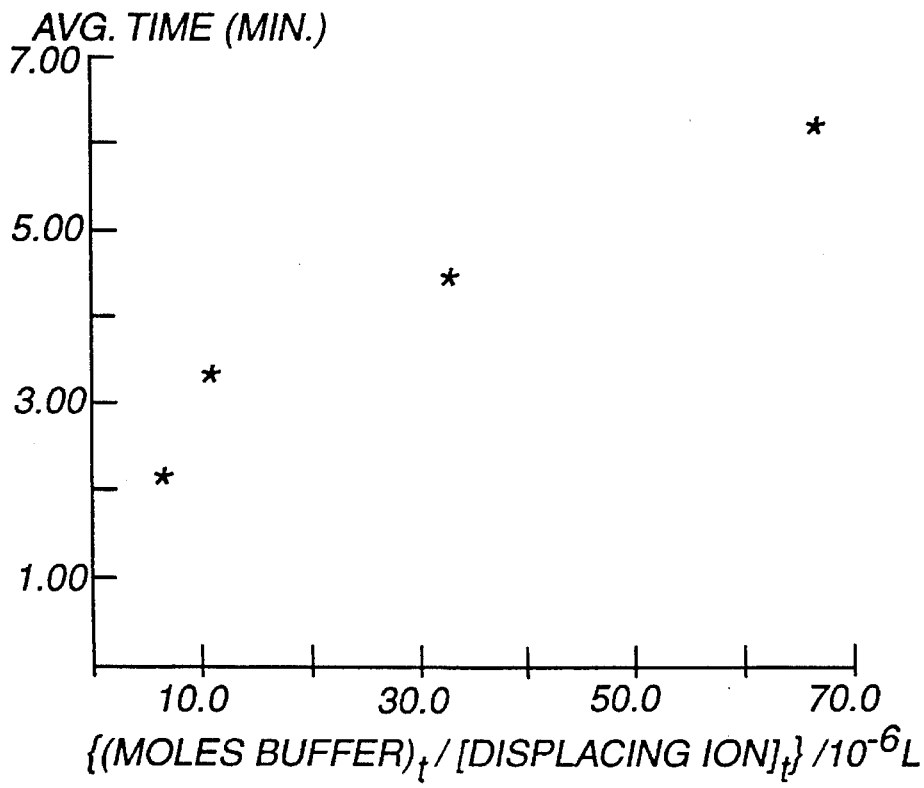
FIG. 10 illustrates a plot of average titration times versus the ratio (total moles buffer)/[total displacement ion concentration] for systems containing serum.

Serum contains numerous cations which can partake in the ion exchange process and several buffer systems which can change the buffering ability of the solution to cover a wider pH range. Therefore, it becomes necessary to modify the relationship between titration time and the quantity (moles of Phosphate Buffer)/[Total Exchangeable Displacing Ion] to take into account the contributions made by the serum. The relationship becomes $$t \alpha k\{[Buffer]_d V_d + [Buffer]_s V_s\}/([Displacing\ Ion]_d + [Displacing\ Ion]_s) \quad (7)$$

where [Buffer] is the concentration of buffer, V is the volume of the buffer to be titrated, and [Displacing Ion] is the equivalent concentration of displacing ions that can take part in the ion exchange process. The subscripts d and s refer to the contributions made by the diluent (solution) and serum respectively. FIG. 10 was constructed using the experimental data for determining serum effects. The experimental contributions for FIG. 10 were addition of 0, 10, 50, and 100 µL of serum to 100 µL of 1:1 0.6M KCl/0.05M Trizma buffer. The plot is linear and the calculated correlation coefficient is 0.972. It can be concluded that the new ratio adequately describes the contributions the final solution makes to the overall timing scheme.

The kinetics of the device depicted in FIGS. 5 and 6 depend largely on the diffusion of inhibitor ion and displacing ion through solution, through the filter 16 or 21, and in the ion exchange membrane 19 or ion exchange bed in cavity 14. The overall rate of diffusion depends on the diffusional path length which is determined by the thickness of the solution film and the thickness of the filter 16 or 21. As ions diffuse in the device, they encounter three distinct environments: an aqueous solution, a porous filter, and an electrostatically charged polymeric membrane. Therefore, one can reasonably conclude that the rate of diffusion depends on the series of diffusional processes which concurrently determine the kinetics of the device.

Ion diffusion is subject to the restriction of electroneutrality. The principle of electroneutrality requires that steps 1–7 in FIG. 7 occur nearly simultaneously at equal rates.

It is believed that the rate determining step of the device is the result of two diffusional processes. The first process is the diffusion of inhibitor ion, for example, $H^+$, through the filter. By increasing the filter thickness, l, the path length increases which in turn increases the time it will take $H^+$ to titrate the buffered solution. The Einstein equation $$l^2 = 2Dt \quad (8)$$

can describe this. D is the diffusion coefficient for the coupled diffusion of $H^+$ and $K^+$ and t is the average time it takes $H^+$ to reach the buffered solution. Equation 8 can be used to determine how the time is altered by changing the thickness of the filter. For example:

$$l_2^2/l_1^2 = 2Dt_2/2Dt_1 \quad (9)$$

where 1 and 2 signify 2 different filter thicknesses. For instance, if $l_1 = 1$ cm and $l_2 = 2$ cm, then equation 9 reveals that by doubling the thickness of the filter the titration time will be increased by four times.

Preliminary experiments show that the theory holds approximately. The results are shown in Table 2.

TABLE 2

The Influence of Filter Thickness on the Titration

| 1 Filter (120 um) Titration Time (min) | 2 Filters (240 um) Titration Time (min) |
|---|---|
| 4.12 | 14.90 |
| 3.44 | 11.05 |
| 4.52 | 14.40 |
| 4.22 | 12.75 |
| 4.10 | 13.65 |
| AVG. 4.08 | AVG. 13.35 |

Experimental Conditions:
[KCl] = 0.03M
[Phosphate buffer] = 0.05M
Total Volume = 100 uL?

The experimental conditions were identical with the exception of filter thickness. The filter thickness for the first set of titration runs was 120 um and 240 um for the second set of runs. The average titration time was calculated from results obtained to be:

$$t/min = 3.09(\pm 0.23)n^2 + 0.99(\pm 0.68) \quad (10)$$

where n=the number of filters. The ratio of these averages reveals that when the filter thickness is doubled, the titration time is 3.27 times longer. Since this value of 3.27 is quite close to the theoretical value of 4, it is concluded that the filter thickness directly influences the rate of the overall ion exchange process and therefore, is said to be rate limiting. The constant term must be the contribution from diffusion in the sample volume, diffusion in the ion exchange membrane and ion exchange kinetics. The lumped contribution from these processes is less significant than the diffusion through the filter.

One can now combine the result from the spacer study with the chemical studies to yield an equation defining the titration time. The equation for calculating the time (minutes) it takes to titrate the buffered solution is as follows:

$$t = k(3.09\, n_f^2 + 0.99)\{(\text{Total Moles Buffer})/[\text{Total Displacing Ion}]\} \quad (11)$$

In this equation, the quantity (Total Moles Buffer) is the total number of moles of buffer (serum+buffered solution) to be titrated and the total displacing ion concentration that can partake in the ion exchange process is represented by [Total Displacing Ion]. The quantity $n_f$ represents the number of filters employed. Finally, k represents a proportionality constant which takes into account the coupled diffusion coefficient which is viscosity and temperature dependent and other contributions made by the solution, the filter, and the membrane that for simplicity have been neglected.

The rate limiting step in the titration is diffusion (see below), which means that the titration time may also be controlled by controlling the viscosity of the reaction solution, according to the Stokes-Einstein equation:

$$D \sim \frac{RT}{6\pi \eta r} \quad (12)$$

In order to increase the viscosity, thereby making the titration time more temperature dependent, glucose, other sugars, and glycols may be used. The rate of diffusion is larger, and consequently titration time is lower, when temperature is higher. This is advantageous since the rate of the reaction being catalysed is also temperature dependent. The reaction rate increases and therefore color intensity increases (at constant titration time) when temperature increases.

Also, because reaction rates are temperature dependent, a normal enzyme level may appear elevated at high ambient temperatures, and an elevated enzyme level could appear normal at low ambient temperatures.

The present invention solves the temperature dependence problem with a built-in temperature compensation means.

Figure 1:
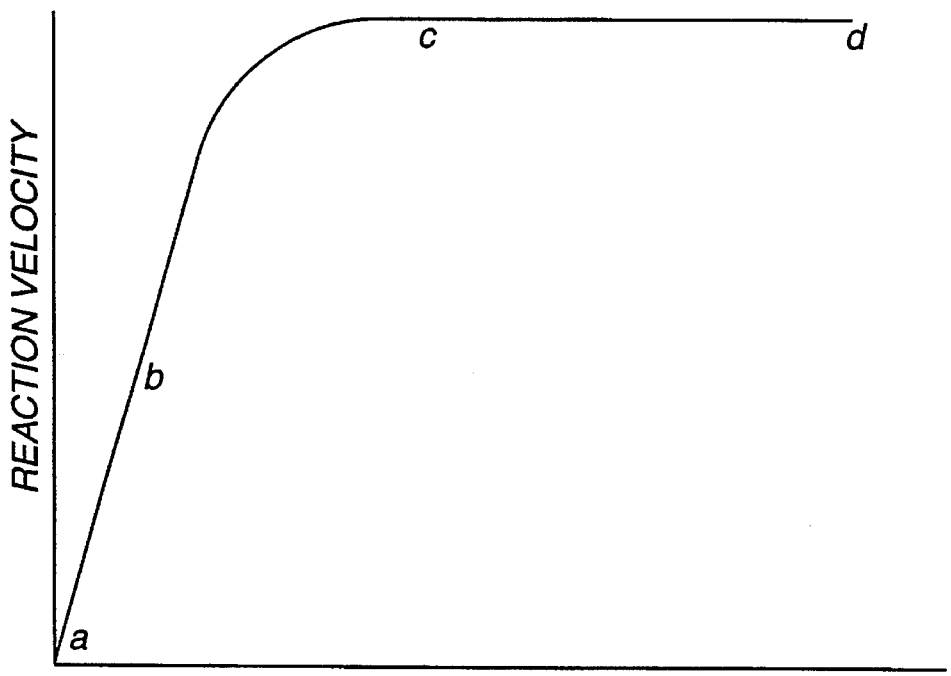
FIG. 1 is a plot of reaction velocity as a function of substrate concentration in which first order and zero order kinetics are defined.
Figure 2:
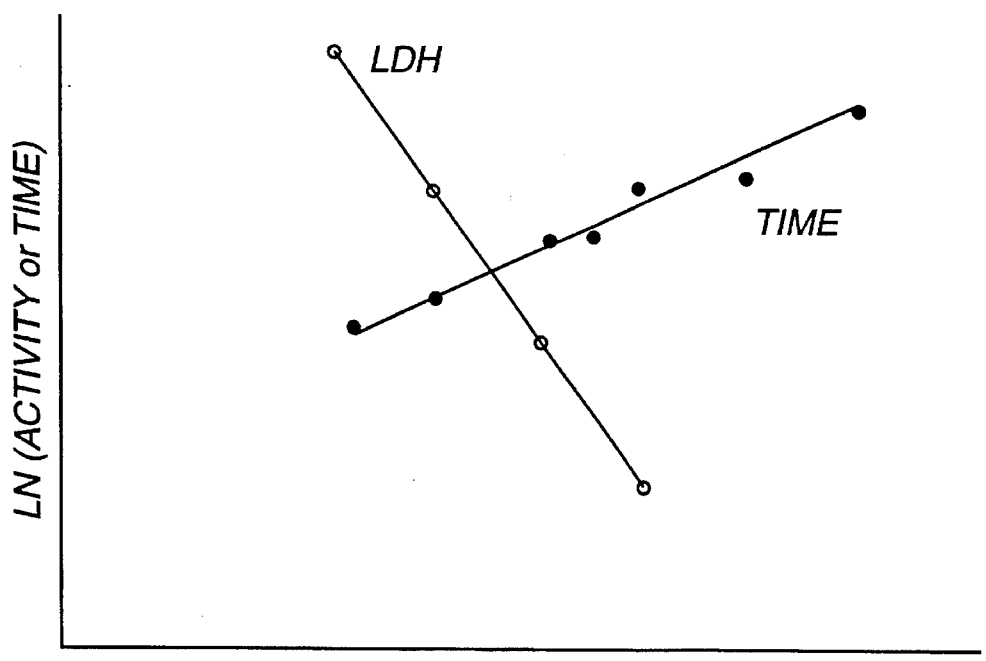
FIG. 2 is a log-log plot illustrating enzyme activity and fuse "length" as a function of temperature for an enzyme-catalyzed reaction.

FIG. 2 shows a log-log plot of LDH activity vs. temperature and "fuse", or titration time vs. temperature for the reaction shown in equation 13. Because enzyme activity increases with increased temperature, while fuse time decreases with increased temperature, it is possible, by altering the system, to produce a constant reaction product concentration, as measured at the end of the titration time, at all temperatures for a given enzyme level by changing the slope of either the activity or time curve or both in FIG. 2 such that the sum of the slopes of the curves equals zero. At that point, the result will be temperature independent, meaning that at high temperatures, high enzyme activity will be precisely compensated for by short titration (reaction) times, and at lower temperatures, lower enzyme activity will be precisely compensated for by longer titration (reaction) times. Thus, for a given quantity of enzyme, a constant quantity of product will be formed regardless of the temperature under which the reaction occurs.

One method of altering the slope of the line for the titration time in FIG. 2 in order to make the slope steeper and thus sum to zero with the LDH slope, is to add glucose, or other sugars, or glycol to the solution to increase solution viscosity (e.g. see H. J. V. Tyrrell and K. R. Harris, *Diffusion in Liquids*, Butterworth's, London, 1984.

Optimization of color Reaction

The enzyme system chosen for the color studies was lactate dehydrogenase (LDH). LDH catalyzes the interconversion of lactate and pyruvate with $NAD^+$ as the hydrogen acceptor. The overall enzymatic reaction is shown as follows:

$$CH_3CHOHCOOH + NAD^+ \underset{\longleftarrow}{\overset{LDH}{\longrightarrow}} CH_3COCOOH + NADH \quad (13)$$

Lactate                        Pyruvate

The pH optimum for the forward reaction

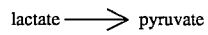

lactate $\longrightarrow$ pyruvate falls between pH 10 and 8.8. For this set of experiments, the pH is always maintained in this region. This insures that the degree of catalytic activity remains constant while adjusting the parameters of the color reaction. Observations of color intensity were made at two and five minutes.

The first task in optimizing the color scheme was to list all possible combinations of buffer (contains $NAD^+$), serum, phenazine methasulphate (PMS), and Nitro Blue Tetrazolium (NBT) (dye). A four factor, two level design is summarized in Table 3 and each of these 16 possibilities was investigated experimentally. The high and low values were determined after preliminary experimentation. The high and low values are done either in terms of concentration or volume. The final volume was 200 uL. PMS and NBT solutions contain 0.2% Triton. Triton prevents side reactions from occurring and prevents the formazan from precipitating.

TABLE 3

Four Factor-two level factorial design for Optimizing the Color Scheme and Their Experimental Results

| | LOW BUFFER [volume] <50 uL | | HIGH BUFFER [volume] ≧50 uL | |
|---|---|---|---|---|
| | LOW PMS 0.078 mmol/L | HIGH PMS 0.81 mmol/L | LOW PMS 0.078 mmol/L | HIGH PMS 0.81 mmol/L |
| LOW DYE 0.31 mmol/L | | | | |
| LOW SERUM <50 uL | 1 − | 2 − | 3 − | 4 − |
| HIGH SERUM ≧50 uL | 5 +,− | 6 − | 7 +,− | 8 + |
| HIGH DYE 0.46 mmol/L | | | | |
| LOW SERUM <50 uL | 9 − | 10 − | 11 − | 12 − |
| HIGH SERUM ≧50 uL | 13 +,− | 14 − | 15 +,− | 16 + |

Each cell of the table contains either a (−), (+), or (+,−) sign. These signs indicate whether or not a color difference between normal and elevated levels of serum was obtained. The (−) sign indicates that no distinct color difference was found. The combinations which yielded a distinct visual difference between levels are denoted by a (+) sign. Those combinations which showed a color difference but to a lesser extent are denoted by a (+,–) sign.

Table 3 shows that the requirements for distinguishing color formation in the presence of measurable enzyme activity are high buffer volume and high PMS concentration (0.81 mmol/L). Other combinations yielded unsatisfactory results, or in the case of dye concentration, were independent of the dye concentrations used.

It is important to point out that conditions have been found such that an easily visible difference between elevated and normal sera is obtained without the aid of specifically removing a quantity of enzyme corresponding to the medical decision level. Thus, in principle, the greatest sensitivity of the test can be obtained by removing a quantity of enzyme from a sample that is equal to a medical decision level. Normal control serum contains, for example, 150 IU of enzyme whereas elevated serum contains 350 IU. By removing 150 IU from each, the levels would then be 0 IU and 200 IU, respectively. The formation of color from a sample containing 200 IU would be clearly distinguishable from that containing 0 IU under virtually any circumstances. The sensitivity of the test to the health of the patient from whence the sample came is therefore quite high. The means to remove 150 IU of enzyme, which would be done by antibody binding, involves additional manufacturing and stability complications. It is thus significant that good sensitivity to an elevated level of LDH can be obtained by optimization of conditions.

ALTERNATE EMBODIMENTS

Figure 12:
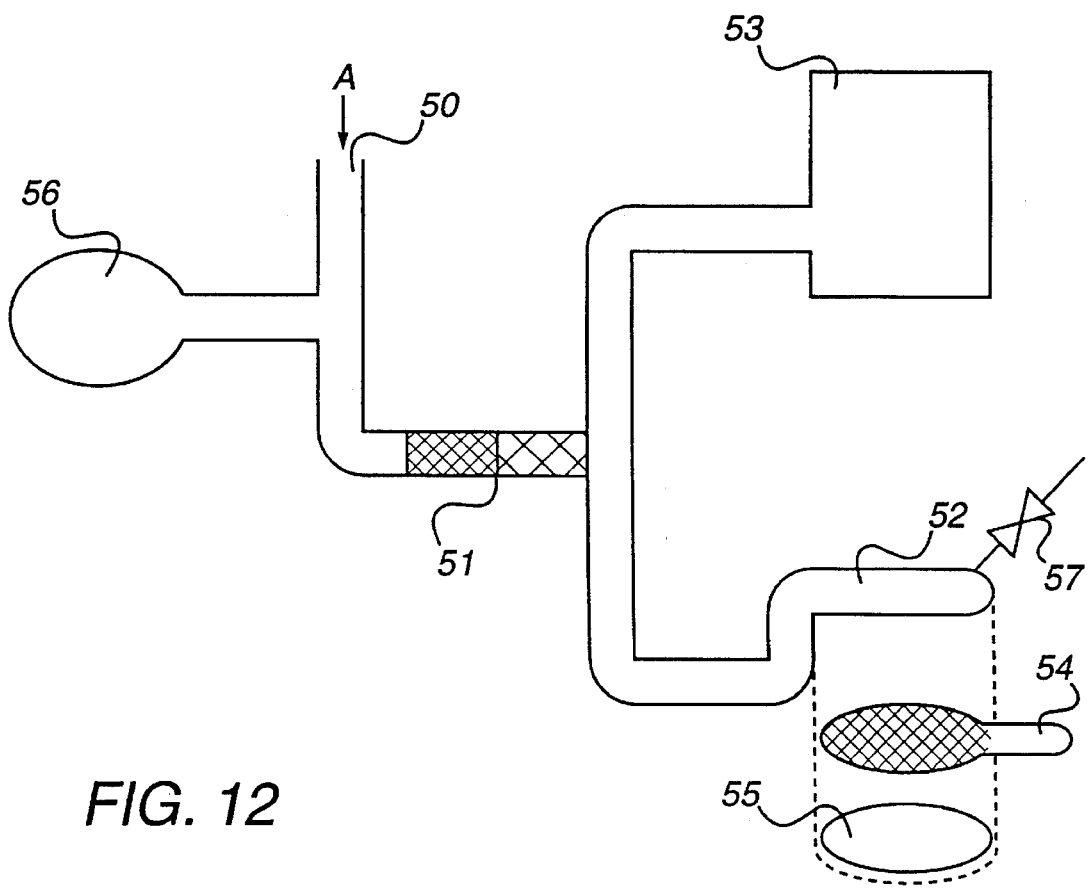
FIG. 12 illustrates a most preferred embodiment of the present invention.

The current apparatus is configured for use in a laboratory, and adequately proves principle. However, devices that operate in the field will be somewhat different. These would preferably include a breakable ampoule with inorganic components (aqueous buffer and displacement ion, such as KCl, $NHa_2PO_4$ and $H_2NaPO_4$), and a capillary means of sampling (such as that of U.S. Pat. No. 3,799,742 by Charles Coleman), as illustrated in FIG. 12. The ampoule would also preferably contain an appropriate concentration of ethylene glycol, glycerol or other means for adjusting the viscosity of the reagent solution to the correct value. As illustrated, the sample A is placed in a sample receiving end 50 and passes through a red blood cell filter 51. The sample may need to be pushed through with a rubber bulb 56, requiring the orifice 50 to be temporarily covered, and requiring a check valve 57 to allow air to escape. After the sample passes through the red blood cell filter 51, the ampoule 53 is crushed, causing the aqueous solution containing buffer, displacing ion and the inorganic species to mix with sample and wash to the filter 52. Components 52, 54 and 55 comprise the reaction vessel in which the enzyme reaction, and the titration for timing control, occur. These components collectively are functionally equivalent to the cells pictured in FIGS. 5 and 6. The filter 52 contains, in dry form, the organic reagents, e.g. substrate and color reagents, required for the enzyme test. A separator means, such as aluminum foil, 54, is positioned between the filters 52 and ion exchange means 55. The separator means 54 is removed, activating the reaction between the ion exchange means 55 and the reagents on the filters 52.

PRECISION

Any such device should be manufactured in such a way so as to maximize the precision of the enzyme assay. It is with this in mind that we have carried out studies of the precision of the titration time. Knowing the sources of imprecision will allow the rational construction of apparatus that are precise.

Precision is a measure of the reproducibility of experimental results. Statistics such as the standard deviation and the variance measure the degree of precision. It is with these parameters that the titration times for 5 sets of data differing only in KCl concentration were examined, All of the data can be found in Table 4.

TABLE 4

The Results Used for Determining the Reproducibility of the Device

| Data Set | Run | [KCl] Mol/L | Titration Time (min) |
|---|---|---|---|
| 1 | 1 | .30 | 2.13 |
|   | 2 |     | 1.88 |
|   | 3 |     | 2.91 |
|   | 4 |     | 2.34 |
|   | 5 |     | 1.80 |
| 2 | 1 | .24 | 3.59 |
|   | 2 |     | 2.20 |
|   | 3 |     | 2.30 |
|   | 4 |     | 2.10 |
|   | 5 |     | 2.74 |
| 3 | 1 | .18 | 2.94 |
|   | 2 |     | 3.04 |
|   | 3 |     | 3.66 |
|   | 4 |     | 2.55 |
|   | 5 |     | 3.05 |
| 4 | 1 | .12 | 3.92 |
|   | 2 |     | 3.10 |
|   | 3 |     | 3.70 |
|   | 4 |     | 3.59 |
|   | 5 |     | 3.72 |
| 5 | 1 | .06 | 4.12 |
|   | 2 |     | 3.44 |
|   | 3 |     | 4.52 |
|   | 4 |     | 4.22 |
|   | 5 |     | 4.10 |

The mean, the standard deviation, and the variance were calculated for each data set. These values can be found in Table 5. The variability among titration times was estimated to be ±0.443 minutes or ±27 seconds.

Figure 11:
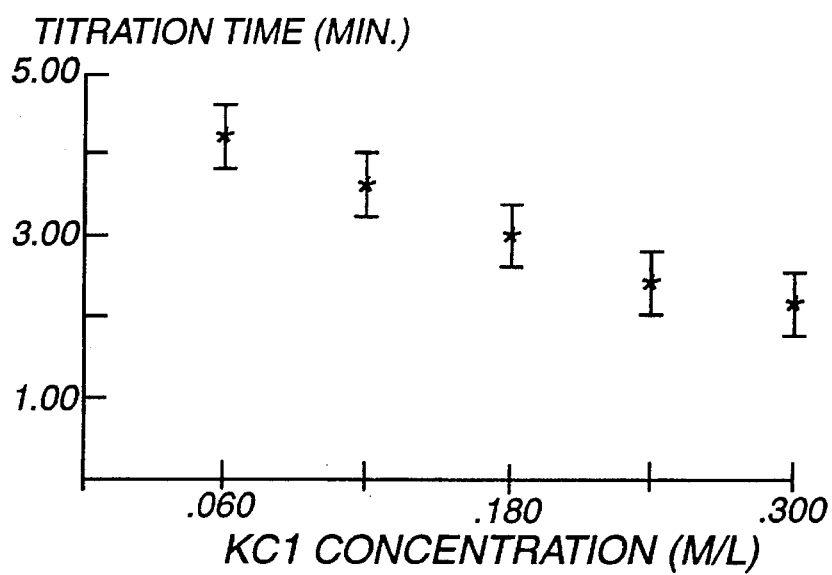
FIG. 11 illustrates a plot of titration time versus KCl concentration, including error analysis for a system according to a preferred embodiment of the present invention.

Another way of looking at the degree of precision is to determine the amount of error present in each measurement. This is shown graphically in FIG. 11. Note that the error appears constant, thus longer titration times will lead to less relative error. The percent error relative to the mean was found to range from 8.6 to 24.6%. Ideally, an acceptable degree of error for clinical enzyme testing devices is around 10%. Therefore, it is necessary to identify all possible sources of error and at best, minimize these errors so that the degree of precision increases to an acceptable level.

TABLE 5

The Mean, the Standard Deviation, and the Variance for Data Sets 1–5.

| Data Set | Mean minutes | Standard Deviation minutes | Variance minutes$^2$ |
|---|---|---|---|
| 1 | 2.21 | ±0.444 | 0.197 |
| 2 | 2.59 | ±0.612 | 0.375 |
| 3 | 3.05 | ±0.398 | 0.158 |
| 4 | 3.61 | ±0.307 | 0.094 |
| 5 | 4.08 | ±0.395 | 0.156 |

The precision in timing is believed to be limited by three general sources: instrumental, device design, and procedure. The errors associated with each source are listed in Table 6. Entries with an asterisk (*) are sources that are unique to the research laboratory and would not influence a working device.

Table 6. Probable Error Sources

A. Instrumental
 1. Measuring and delivering small sample sizes such as 100 uL
  —variations in final volume delivered?
 *2. Response time between meter and recorder
  —time lag?
B. Device Design
 1. Variations in cell construction
  —cell leaks?
 2. Secure fit between the filter and Nafion membrane
  —filter buckling, leaving an undefined amount of space between the two?
C. Procedure
 *1. Position of electrodes in regards to the solution and filter
  —electrodes always touching the surface of the filter?
  —measuring pH changes precisely at the same location each time?
 2. Filter
  —porosity cause for fluctuations?
 *3. Rinsing the cell before each run water layer constant?
 4. Counterion Concentration
  —too concentrated such that the titration time is actually faster than the recorded titration time?
 *5. Choice of endpoint
  —stopping at pH 2.5 a good choice?

Preliminary experiments were performed to determine what contribution if any, these suspected sources of error contributed to the variations in timing. The major source of error was found to lie in the choice of transition point or end point. This is one of the sources that is only met in the research lab; in the field the pH is not measured. It was found that it is not necessary to monitor the titration to a pH of 2.5. Reexamination of the titration curves indicated that pH 4 is a more suitable stopping point because the buffered solutions were completely titrated by pH 4. To justify further this choice, the titration times were measured for both points using the titration curves from Data Set 3 in Table 4 and their results can be found in Table 7. The percent error in this case decreased from 13% to 9% when ending at pH 4. As a result, the precision in timing increased.

TABLE 7

Effect on Precision by Changing the pH
Range in Which the Titration is Monitored*

| Run | pH 8 to pH 4 Titration Time (minutes) | pH 8 to pH 2.5 Titration Time (minutes) |
| --- | --- | --- |
| 1 | 2.06 | 2.94 |
| 2 | 2.34 | 3.04 |
| 3 | 2.38 | 3.66 |
| 4 | 1.92 | 2.55 |
| 5 | 2.30 | 3.05 |

*Experimental Conditions
[KCl] = 0.18M
[Phos. Buffer] = 0.05M
Total Volume = 100 uL

OTHER SYSTEMS

The above disclosure demonstrates that the present invention is capable of noninstrumentally controlling the time during which an enzymatic reaction, for example (Lactate $\xrightarrow{LDH}$ Pyruvate), is allowed to proceed. The invention allows the discrimination of various activity concentrations of lactate dehydrogenase. A mathematical model based on theoretical considerations as well as experimental results adequately describes what factors are responsible for controlling the time. This model provides a basic understanding which can be applied to other enzyme systems, such as binding assays, including immunoassays and immunometric assays, which rely on enzyme determinations.

Other inhibiting ions may be employed although the sensitivity of enzymes to $H^+$ is ubiquitous. Hydroxide ion has been successfully used with a layer of ion exchange resin, rather than a sheet of ion exchange membrane. Chloride in the sample becomes the displacing ion. The enzyme Lactate Dehydrogenase (running in the reverse direction from that in Equation 13) was used to establish the viability of a base-going fuse. This would be appropriate for other enzymes with base sensitivity such as acid phosphatase.

Many enzymes including acetylcholinesterase (E.C. 3.1.1.8) are susceptible to inhibition by specific organic compounds, many of which are nitrogen bases. We have found that the inhibitor quinidine can be used in the following way. In place of an ion exchange membrane one places a paste of the water-insoluble free base (quinidine), with ion exchange resin beads in the $H^+$ form. Potassium ions act as displacing ions, displacing $H^+$, but the $H^+$ protontates a molecule of the basic inhibitor quinidine which then diffuses through the filter into the enzyme-containing reaction chamber. In this way, the concentration of inhibitor increases, eventually turning off the enzyme.

Another embodiment would employ chelating agents in either of two ways. Chelating agents have been bound to particles to form chelating resins. This would replace the ion exchange resin in the preferred embodiment. Since many enzymes require dication (creatine kinase requires $Mg^{2+}$ for example) one can use the timing scheme to remove an activator rather than to add an inhibitor. Ions of $Mg^{2+}$ would be pulled into the chelating resin stopping enzyme activity.

Chelating agents could also be used as titrants, analogous to $H^+$, except that most commonly chelating agents are anionic. Thus, an anion exchange resin would hold an anionic chelator. An ion such as Cl− would be the displacing ion. An analogy to the buffer would be an ion that was more tenaciously bound by the chelator than the activating ion.

Thus, the chelator would diffuse into the sample side of the solution at a rate that depends on quantities discussed above. It would first chelate the buffer ion. When the buffer ion is exhausted, the activator ion (such as $Mg^{2+}$ for creatine kinase) is chelated, and the enzyme stops.

Table 8 gives a general overview of the various chemistries that can be used. A chemistry must be chosen depending on the properties of the enzyme of interest.

It is clear that the present invention can be used in other applications. Any catalytic system whose rate must be determined can be controlled by this means as long as the presence of the solvent does not destroy the enzyme activity. The solvent need not be water. It is possible to use the timing scheme to determine substrate concentrations. One must operate in the region where the reaction is not zero order in substrate.

One can use the device to indirectly control the entry of a substance into any enclosed space for any purpose. Thus a membrane whose permeability or structural integrity is sensitive to some ionic species may be caused to become more permeable or disintegrate after a given time based on the timing device described herein. Thus virtually any two solutions can be caused to mixed after a given time.

The device can be used in a fashion in which the functions of the various components are altered. Thus, we have described the use of the timing device for determining a reaction rate based on a color change. It can equally well be used to determine viscosity, quantity of buffer, or concentration of displacing ions. Thus, an enzyme or other ion-sensitive catalyst is present at a constant activity. The solution about which information is desired is mixed with a known quantity of solution containing catalyst and required substrate and reagents in a device such as that described herein. The reaction rate is constant since the quantity of catalyst is constant. However the time that the reaction is allowed to occur is under control of the properties of the unknown solution. Thus the salinity of water could be determined. Higher salinity would be a higher concentration of displacing ion which would result in a lower time (equation 15). Likewise, viscosity or the quantity of buffer (where the meaning of buffer is quite general, see Table 8) can also be determined in this way.

Table 8 illustrates the various combinations of inactivators and buffers for particular enzyme applications.

TABLE 8

| Inactivator | Buffer (Optional) | Enzyme Property |
| --- | --- | --- |
| $H^+$ | base | pH sensitivity |
| $OH^-$ | acid | pH sensitivity |
| anions, chelators, ligands | metal ion | specific binding of anion; requirement for a metal ion whose activity is lowered by the anion |
| metal ions | ligands, chelators, etc. | specific binding of metal ion, e.g. to a lysine or histidine sensitivity to this specific inhibitor |
| organic inhibitors | antibody, binding agent | sensitivity to this specific inhibitor |

Although the invention has been described in detail in the foregoing for the purpose of illustration, it is to be understood that such detail is solely for that purpose and that variations can be made therein by those skilled in the art without departing from the spirit and scope of the invention as described by the claims. For example, although the present invention may be used for measuring enzyme activities without the need for an instrument, it is anticipated that those skilled in the art would be able to utilize the chemical fuse and/or temperature insensitivity aspects of the device in combination with a traditional product sampling instrument for performing enzyme assay.

I claim:

1. A method of performing a non-instrumental test in a test device to determine the presence of an enzyme in a liquid biological sample wherein said enzyme is present in an amount above a predetermined critical level where the critical level distinguishes an abnormal condition from a normal condition, comprising the steps of:

a. placing the sample in contact with a reacting medium in said test device, the reacting medium containing at least one reagent for producing a visible by-product, said reacting medium being in communicative connection with at least one reagent for modulating enzyme activity contained in the sample to limit time of reaction to a predetermined reaction time;

b. reacting reagents of said reacting medium to form a reaction product in said test device, said reaction product being formed by a reaction catalyzed by said enzyme under conditions favoring formation of said product; and c. reacting said reaction product according to a second reaction which produces the visible by-product in said test device when the amount of said enzyme in said sample exceeds said critical level.

2. The method of claim 1 wherein said enzyme reacts according to a dehydrogenase reaction including nicotinamide adenine dinucleotide as a reagent of said reacting medium, said reaction product including a reduced coenzyme of said nicotinamide adenine dinucleotide which reacts according to step (c) to form said visible by-product.

3. The method of claim 1 further comprising removing an amount of said enzyme corresponding to said critical level from said sample whereby said reagents are used to determine the presence of any residual said enzyme remaining in said sample.

4. The method of claim 1 wherein said test is selected from the group consisting of enzyme-linked and enzyme immunoassays.

5. A method of performing a non-instrumental test in a test device in order to determine the presence of an enzyme in a sample wherein said enzyme is present in an amount above a predetermined critical level, comprising the steps of:

a. placing said sample in contact with a reacting medium in a test device, said reacting medium being positioned adjacent a spacer means for effecting a diffusion barrier in said test device, said spacer means being positioned adjacent an ion exchange means in said test device, such that said spacer means separates said reacting medium from said ion exchange means, said ion exchange means containing a predetermined quantity of enzyme inactivating ions, which ions inactivate catalytic effects of said enzyme;

b. reacting reagents of said reacting medium in a solution containing said enzyme and displacing ions, said enzyme causing a reaction of said reagents to form a product in said test device according to a reaction catalyzed by said enzyme, said displacing ions diffusing through said spacer means in one direction towards said ion exchange means, and displacing said inactivating ions from said ion exchange means, said displaced inactivating ions diffusing through said spacer means in an opposite direction relative to said displacing ion direction, said displaced inactivating ions traveling through said spacer means and inactivating said catalytic effects of said enzyme, thereby terminating said reaction after a predetermined reaction time; and c. determining the amount of said product formed by said reaction in said test device and determining whether said amount of said product corresponds to a level of said enzyme in said sample exceeding said predetermined critical level.

6. The method of claim 5 wherein said amount of said product is determined using a directly reacting chromogenic indicator, which indicator produces a visible change in said solution when said product is formed in amounts corresponding to an enzyme level in said sample exceeding said predetermined critical level.

7. The method of claim 6 wherein said reagents include a reducible dye and said visible change is a color change in said solution produced by said enzyme catalyzing said reaction in the presence of a reducible reagent suitable for reducing said dye, whereby reduction of said reducible reagent enables said reducible reagent to reduce said dye to produce said visible color change.

8. The method of claim 7 wherein said reducible reagent transfers H to said dye via an electron carrier.

9. The method of claim 7 wherein said electron carrier is 5-methylphanazinium methyl sulphate.

10. The method of claim 7 wherein said dye is a tetrazolium salt which is reduced to a formazan to produce said visible color change.

11. The method of claim 6 wherein said enzyme is lactate dehydrogenase and said product is pyruvate.

12. The method of claim 5 wherein the said solution contains a buffer means.

13. The method of claim 5 wherein said inactivator ions are selected from the group consisting of $H^+$, $OH^-$, and metal ions.

14. The method of claim 5 wherein said reaction proceeds such that the amount of said product formed prior to said reaction being stopped by said inactivator is a function of the sample enzyme level and wherein the effect of the ambient temperature under which said reaction occurs is decreased by controlling diffusion rates of said displacing ions and said inactivating ions through said displacer.

15. The method of claim 14 in which the effect of the ambient temperature under which said reaction occurs is decreased by adjusting the viscosity of said solution at the time of manufacture of said test device.

16. The method of claim 15 wherein said viscosity adjustment is accomplished at the time of manufacture of said test device by adding an additive to increase viscosity of said solution without adversely affecting said reaction, said additive being selected from the group consisting of sugars and glycols.

17. The method of claim 5 wherein said reagents exist in a dry form on or in said reacting medium.

18. The method of claim 5 wherein said reagents are added to said reacting medium prior to adding the sample.

19. The method of claim 5 wherein said determination of said product is accomplished by an absorption spectrometry analyzer means.

20. The method of claim 5 wherein said inactivating ions are chelating agents.

21. The method of claim 5 wherein said inactivating ions are ligands.

22. A method for non-instrumentally controlling reaction time of a chemical reaction in a test device to determine if an amount of an enzyme in a sample exceeds a predetermined level, wherein the enzyme is employed in a solution within said test device to favor formation of one or more products from one or more reactants participating in said reaction, said method comprising, controllably releasing an enzyme inactivator means contained within said test device into the solution wherein said reaction occurs, said inactivator means being controllably released so as to substantially inactivate said enzyme and thereby substantially halt said reaction after a predetermined time.

23. The method of claim 22 wherein said inactivator means comprises inactivating ions.

24. The method of claim 22 wherein said solution contains buffer means for regulating the concentration of said inactivator means.

25. The method of claim 22 wherein said solution is initially separated from said inactivator means by a spacer means, which regulates the flow of said inactivator means to said solution.

26. The method of claim 25 wherein said inactivator means comprises inactivator ions, and said solution includes displacing ions therein, said displacing ions diffusing through said spacer means away from said solution, thereby displacing said inactivator ions from a medium holding said inactivator ions, said displaced inactivator ions diffusing through said spacer means toward said solution, thereby inactivating said enzyme in said solution.

27. The method of claim 26 wherein said medium for holding said inactivator ions comprises an ion exchange means.

28. The method of claim 22 wherein said inactivator means inactivates said enzyme by changing the pH of said solution to a pH at which said enzyme is substantially inactive.

29. The method of claim 22 wherein the effect of the ambient temperature under which said reaction occurs is decreased by controlling the rate of molecular or ionic diffusion.

30. The method of claim 22 further comprising providing said solution with means for indicating presence of said product above a predetermined level.

31. The method of claim 22 wherein said enzyme is present in said solution in a constant concentration and said reactants are present in unknown and variable concentrations.

* * * * *